US007294719B2

(12) United States Patent  
Carubia et al.

(10) Patent No.: US 7,294,719 B2
(45) Date of Patent: Nov. 13, 2007

(54) SYNTHESIS OF AMINO ACID, N-CARBOXYANHYDRIDES

(75) Inventors: John Michael Carubia, Guilford, CT (US); Thomas Mark Weaver, Naugatuck, CT (US); Ettigounder Ponnusamy, Ballwin, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 227 days.

(21) Appl. No.: 11/259,672

(22) Filed: Oct. 26, 2005

(65) Prior Publication Data

US 2006/0106229 A1    May 18, 2006

Related U.S. Application Data

(60) Provisional application No. 60/622,135, filed on Oct. 26, 2004.

(51) Int. Cl.
*C07D 207/12* (2006.01)
*C07C 227/02* (2006.01)

(52) U.S. Cl. ........................ 548/227; 548/229; 562/888

(58) Field of Classification Search ................ 548/227; 562/888
See application file for complete search history.

(56) References Cited

U.S. PATENT DOCUMENTS 3,846,399 A    11/1974    Hirshmann et al.
4,064,218 A    12/1977    Scholz et al.
RE30,170 E     12/1979    Goodman et al.
4,235,942 A    11/1980    Heller et al.
4,238,465 A    12/1980    Chun
4,267,334 A     5/1981    Esteve Subirana
4,493,818 A     1/1985    Gross
4,686,295 A     8/1987    Youssefyeh et al.
4,900,523 A     2/1990    Bicker et al.
4,946,942 A     8/1990    Fuller et al.
5,028,693 A     7/1991    Fuller et al.
5,135,754 A     8/1992    Brack
5,945,558 A     8/1999    Mallow
6,464,951 B1   10/2002    Kittrell et al.
6,479,665 B2   11/2002    Cornille et al.
6,596,664 B2    7/2003    Kittrell et al.
6,603,016 B2    8/2003    Cornille et al.
6,656,458 B1   12/2003    Philippe et al.

*Primary Examiner*—Kamal A. Saeed
(74) *Attorney, Agent, or Firm*—Senniger Powers; Brian K. Stierwalt; Jeffrey Wilson

(57) ABSTRACT

A process for producing N-carboxyanhydrides is disclosed. The process produces N-carboxyanhydrides as a product and HCl as a by-product. The HCl by-product is purged from the reaction mixture by passing a purge gas through the reaction mixture as a carbonylation reagent is reacting with an amino acid or a salt thereof. The N-carboxyanhydrides produced by this process have a relatively lower chloride impurity content, relatively higher yields can be achieved, and the N-carboxyanhydrides can be produced on a larger scale.

30 Claims, 1 Drawing Sheet

SYNTHESIS OF AMINO ACID, N-CARBOXYANHYDRIDES

CROSS-REFERENCE TO RELATED APPLICATIONS

This application is a nonprovisional of U.S. Patent Application Ser. No. 60/622,135, filed Oct. 26, 2004. The entire text of that application is hereby incorporated herein by reference.

BACKGROUND OF THE INVENTION

The present invention is generally directed to the preparation of N-carboxyanhydrides and, more specifically, to reducing or minimizing the chloride content of reaction mixtures in which N-carboxyanhydrides of amino acids are prepared.

N-carboxyanhydrides of amino acids are routinely used in the synthesis of polypeptides. For example, in U.S. Pat. No. 6,656,458, Philippe et al. describe the synthesis of polyamino acids from representative N-carboxyanhydrides such as sarcosine N-carboxyanhydride, threonine N-carboxyanhydride, serine N-carboxyanhydride, valine N-carboxyanhydride, norvaline N-carboxyanhydride, isoleucine N-carboxyanhydride, leucine N-carboxyanhydride, norleucine N-carboxyanhydride, lysine N-carboxyanhydride, phenylalanine N-carboxyanhydride, and tyrosine N-carboxyanhydride.

Several processes are known for preparing N-carboxyanhydrides. One method for producing N-carboxyanhydrides is the reaction of an amino acid or its salt with phosgene in a solvent medium. For example, in U.S. Pat. No. 4,267,344, Halstrom et al. disclose preparing N-carboxyanhydrides, in part, by bubbling phosgene through a solution of substituted amino acids and a solvent. In U.S. Pat. No. 6,603,016, Cornille et al. disclose preparing N-carboxyanhydrides by reacting amino acids with phosgene, diphosgene, or triphosgene in a solvent medium. In U.S. Pat. No. 6,479,665, Cornille et al. disclose preparing N-carboxyanhydrides by reacting amino acids with phosgene, diphosgene or triphosgene in a solvent medium wherein the reaction at least partially occurs in the presence of an unsaturated organic compound which has one or more ethylenic double bonds, the remainder of the molecule being inert to other compounds in the reaction mixture, and one of the carbons of at least one ethylenic double bond of which is completely substituted by substituents other than halogen atoms.

A general reaction scheme for the formation of an N-carboxyanhydride by reaction of an amino acid with phosgene is as follows:

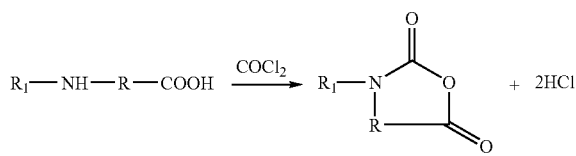

During the formation of an N-carboxyanhydride by reaction of an amino acid or its salt with phosgene, a considerable amount of HCl is also produced. HCl in the reaction medium, in turn, can lead to the formation of chlorinated by-products which remain in the N-carboxyanhydride product, affecting purity and yield. For example, HCl can cause ring opening of tetrahydrofuran (a solvent commonly used in the reaction mixture) leading to the formation of 4-chlorobutyl chloroformate. Chlorinated compounds also affect polymerization reactions of N-carboxyanhydrides, because effective polymerization requires the absence, or a sufficiently low amount, of chlorinated compounds present in the N-carboxyanhydride monomers.

Various approaches have been used to reduce the concentration of HCl and chlorinated derivatives in the reaction product. In U.S. Pat. No. 5,135,754, Brack sweeps the reaction mixture with argon for at least 48 hours at 48° C.; see U.S. Pat. No. 5,135,754 at column 3, lines 50-52. Mallow heats the reaction product (a partial ester) to 40°-60° C. and purges with nitrogen to remove hydrogen chloride; see U.S. Pat. No. 5,945,558 at column 4, lines 38-41. Goodman et al. purge the reaction system with nitrogen for one hour before the reaction is initiated and, following the addition of phosgene, purge the reaction mixture with nitrogen for another two hours; see U.S. Reissue Pat. No. 30,170 at column 5, lines 6-12. In U.S. Pat. No. 6,603,016, Cornille et al. carry out the reaction, at least in part, at a pressure less than 1000 mbar. In general, however, these approaches tend to yield a product having a relatively high chloride content, are not well-suited for relatively large scale production, require a relatively long period of time for the phosgene, diphosgene or triphosgene to react with the amino acid, and/or require a quiescent reaction mixture. Additionally, the intermediate N-carboxyanhydride created during the reaction of phosgene, diphosgene or triphosgene with the amino acid is relatively unstable, and may decompose during the longer reaction time required for large scale production.

SUMMARY OF THE INVENTION

Among the various aspects of the present invention is an improved process for the preparation of N-carboxyanhydrides, in general, and the γ-ethyl ester and the γ-benzyl ester of L-glutamic acid N-carboxyanhydrides, and N6-CBZ-L-lysine, in particular.

Briefly, therefore, the present invention is directed to a process for the preparation of N-carboxyanhydrides. The process comprises forming a reaction mixture comprising an amino acid or a salt thereof, a solvent, and a carbonylation reagent. The carbonylation reagent is selected from the group consisting of phosgene, diphosgene, triphosgene and mixtures thereof. The carbonylation reagent reacts with the amino acid or a salt thereof to yield an N-carboxyanhydride as a product and HCl as a by-product. The HCl by-product is purged from the reaction mixture by passing a purge gas through the reaction mixture as the carbonylation reagent is reacting with the amino acid or a salt thereof. The purge gas is treated after it has passed through the reaction mixture to neutralize the carbonylation reagent therein.

Other objects and features of this invention will be, in part, apparent and, in part, pointed out hereinafter.

DETAILED DESCRIPTION OF THE INVENTION

Figure 1:
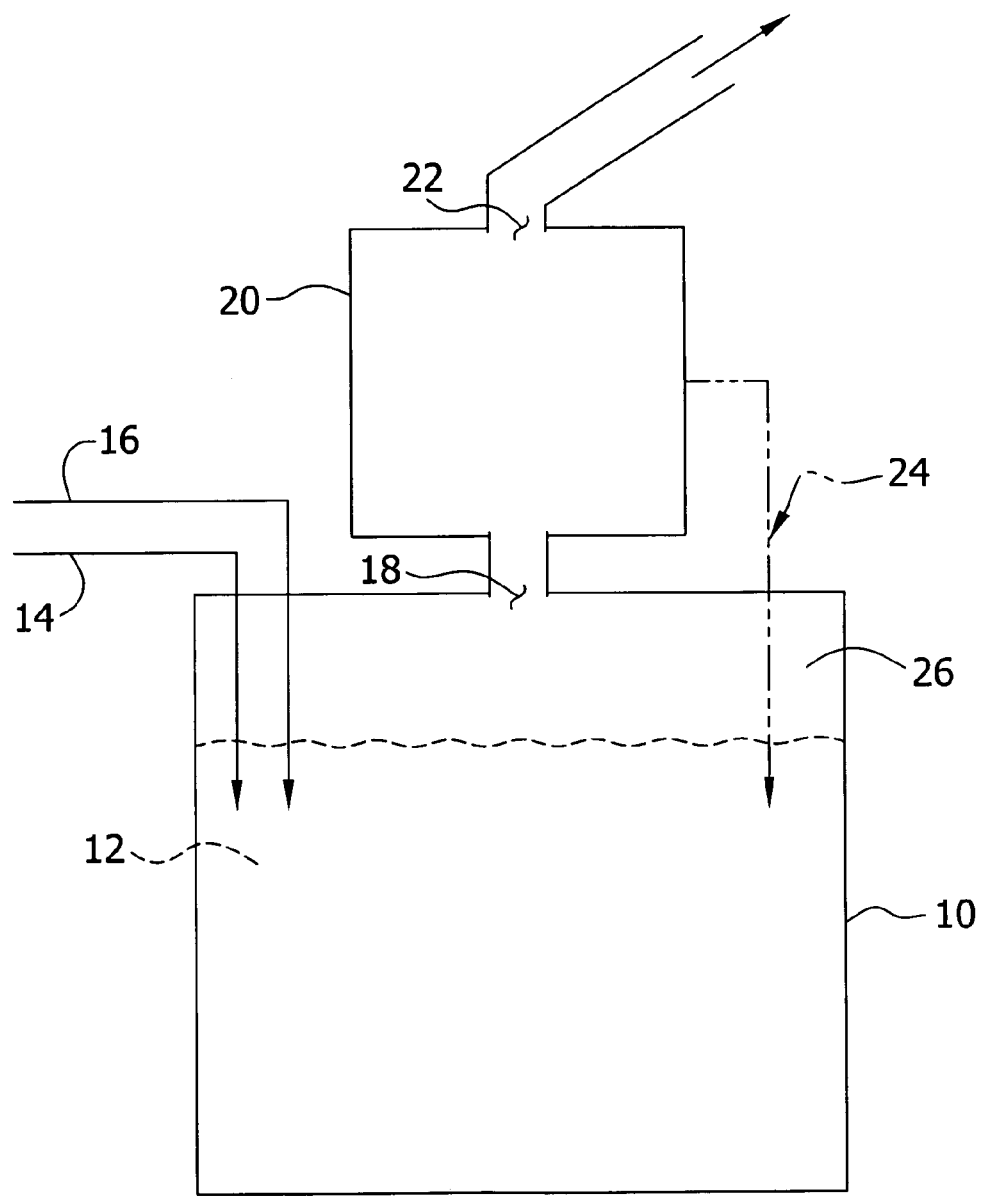
FIG. 1 is a schematic diagram of the reaction vessel, the reaction mixture contained therein, the sparge tubes which are placed below the surface of the reaction mixture, and the treatment apparatus connected to the reaction vessel.

In accordance with the present invention, a reaction mixture is formed comprising an amino acid or a salt thereof, a solvent, and a carbonylation reagent. The amino acid and carbonylation reagent react to form an N-carboxyanhydride product and HCl as a by-product. In a preferred embodiment, the HCl content of the N-carboxyanhydride formed by the reaction of an amino acid or a salt thereof and a carbonylation reagent is preferably less than 0.1% by weight.

In general, the process of the present invention provides a range of advantages. Not only does the purge gas remove hydrogen chloride from the reaction mixture as it is formed, but it also aids in cooling the reaction mixture, allowing the carbonylation reagent to be added at a relatively rapid rate. The purge gas also reduces the concentration of oxygen in the reaction mixture, thereby reducing flammability or the risk of a similar hazard. In addition, relatively large scale batches of N-carboxyanhydrides (e.g., greater than 1,000 g) can be synthesized with at least a 60% yield, and with a chloride impurity content of less than 0.08%. For example, L-glutamic acid N-carboxyanhydride, γ-ethyl ester may be prepared with a yield of at least 65% and a chloride content of 0.02 wt. % or less. Similarly, L-glutamic acid N-carboxyanhydride, γ-benzyl ester may be prepared with a yield of at least 85% and a chloride content of 0.02 wt. % or less. By way of further example, N6-CBZ-L-lysine may be prepared with a yield of at least 85% and a chloride content of 0.08% or less.

Reaction Mixture

In general, any amino acid that is capable of forming an N-carboxyanhydride may be used in the reaction mixture. For example, the amino acid may be glycine, alanine, valine, leucine, isoleucine, phenylalanine, serine, threonine, lysine, Δ-hydroxylysine, ornithine, aspartic acid, glutamic acid, cysteine, cystine, methionine, tyrosine, thyroxine, proline, hydroxyproline, tryptophan, or a salt or derivative thereof. By way of another example, the reaction mixture may be prepared using a salt such as the sulphate, hydrohalide, hydrochloride, or hydrobromide salt of an amino acid. Alternatively, the reaction mixture may be prepared using an amino acid derivative in which the side chain of the carboxyl group is protected with an ester (e.g., a benzyl, p-nitrobenzyl, phenyl, pentachlorophenyl, ethyl or methyl ester), or an amino acid derivative in which the side chain of the amino group is protected with an amino protecting group. Such amino protecting groups may be selected, for example, from the group consisting of benzyloxycarbonyl (CBZ), 2-(4-biphenylyl)-2-propyloxycarbonyl (Bpoc), 2-bromobenzyloxycarbonyl, p-toluenesulfonyl, 4-methoxybenzenesulfonyl, 2-chlorobenzyloxycarbonyl, 2-nitrophenylsulphonyl, 4-toluenesulphonyl, and the like.

In one preferred embodiment, the reaction mixture comprises the γ-benzyl ester of glutamic acid, the γ-ethyl ester of glutamic acid, N6-CBZ-L-lysine or a salt thereof.

The reaction mixture also contains a solvent or a solvent system (i.e., a mixture of solvents). Exemplary solvents include ethereal solvents such as tetrahydrofuran, dioxane, diethyl ether, and isopropyl ether; chlorinated solvents such as dichloromethane, chloroform, and 1,2-dichloroethane; polar aprotic solvents such as N,N'-dimethylformamide, acetonitrile, and acetone; or alkyl acetates such as ethyl acetate, and combinations thereof.

In general, the carbonylation reagent is selected from the group consisting of phosgene, diphosgene, triphosgene and combinations thereof. Diphosgene is a relatively toxic, lachrymating liquid and, as a result, is generally not preferred because of associated material handling issues. Triphosgene is less expensive than phosgene, but it is a relatively toxic solid and, as a result, is also generally not preferred because of associated material handling issues. In contrast, phosgene can be readily introduced to the reaction mixture at a controlled rate using a metering valve. Phosgene also tends to provide a cleaner, purer product with fewer impurities from side reactions that can occur with diphosgene and/or triphosgene. As a result, phosgene tends to be preferred over diphosgene and triphosgene.

Process Steps

Referring now to FIG. 1, an amino acid or a salt thereof is dispersed in a reaction vessel 10 with a solvent or solvent system to form a reaction mixture 12. A first sparge tube 14 and a second sparge 16 tube are immersed in the reaction mixture 12 whereby gases and/or liquids may be introduced beneath the surface of the reaction mixture 12. The reaction vessel 10 also contains an outlet 18, through which gases may exit the reaction vessel 10. Connected to the outlet 18 is a treatment apparatus 20, preferably a condenser and/or a scrubber. The treatment apparatus 20 has an outlet 22, through which treated gases may exit the treatment apparatus 20. In a preferred embodiment, where the treatment apparatus is a condenser, an inlet 24 is positioned so as to reintroduce condensed carbonylation reagent into the reaction mixture 12. There is typically some amount of vapor-space 26 between the top surface of the reaction mixture 12 and the top of the reaction vessel 10. On a percentage basis, the vapor-space will typically comprise about 30% to about 40% of the reaction vessel volume; in a preferred embodiment, the vapor-space comprises about 30% of the reaction vessel volume.

Preferably, the process of the present invention will be carried out as a batch process. The reaction mixture is formed by adding an amino acid or a salt thereof to a solvent or solvent system in a glass or other suitable reaction vessel with stirring. Initially, the reaction mixture is a slurry of the amino acid or a salt thereof in the solvent or solvent system. The amino acid concentration in the slurry is typically at least about 0.02 M and less than about 1.5 M; preferably, the amino acid concentration in the slurry will be from about 0.6 M to about 1.2 M. For example, where the amino acid is L-glutamic acid, γ-ethyl ester, the amino acid concentration in the slurry is typically about 1.0 M to about 1.2 M. Where the amino acid is L-glutamic acid, γ-benzyl ester, the amino acid concentration in the slurry is typically about 0.6 M to about 0.8 M. Where the amino acid is N6-CBZ-L-lysine, the amino acid concentration in the slurry is typically about 0.4 M to about 1.0 M.

When the carbonylation reagent is in the gaseous state, it is preferably introduced into the reaction mixture using a metering valve and a sparge tube placed at least about 1 centimeter below the surface of the reaction mixture. The sparge tube may be placed at greater depths; solids in the heterogeneous mixture, however, may tend to clog the sparge tube if it is placed too near the bottom of the reaction vessel, particularly in the beginning of the reaction. In one preferred embodiment, a sparge tube is immersed about 5 centimeters below the surface of the reaction mixture and the carbonylation reagent is introduced in the form of a gas. In an alternative embodiment, the carbonylation reagent is introduced as a liquid or as a solid dissolved in a solvent. In a preferred embodiment, the carbonylation reagent is phosgene gas, introduced to the reaction mixture at a rate of about 0.2 moles/min to about 0.8 moles/min.

As the carbonylation reagent is introduced, the reaction mixture is preferably maintained at a temperature of about 50° C. to about 65° C. and at atmospheric pressure. Other temperatures and pressures, however, may be employed.

As previously noted, the reaction of the amino acid substrate and the carbonylation reagent generates HCl as a by-product. This by-product is purged from the reaction mixture by passing a purge gas through the reaction mixture as the HCl is being generated. Exemplary purge gases include helium, nitrogen, neon, argon, and mixtures thereof. In one embodiment, the purge gas is predominantly nitrogen or helium; that is, the partial pressure of nitrogen, helium, or a combination thereof in the purge gas is at least 70%. More preferably, the partial pressure of nitrogen, helium, or a combination thereof in the purge gas is at least 90%. Still more preferably, the partial pressure of nitrogen in the purge gas is at least 99%.

The purge gas is preferably introduced to the reaction mixture at atmospheric pressure through a sparge tube placed at least about 1 centimeter below the surface of the reaction mixture. The sparge tube may be placed at greater depths; solids in the heterogeneous mixture, however, may tend to clog the sparge tube if it is placed too near the bottom of the reaction vessel, particularly in the beginning of the reaction. In one preferred embodiment, a sparge tube is immersed about 7.5 centimeters below the surface of the reaction mixture. Preferably, the purge gas is introduced as the carbonylation reagent is being introduced (and reacts with the amino acid or derivative or salt thereof). In an alternative embodiment of the present invention, however, the purge gas is introduced intermittently during the period of time in which the carbonylation reagent is being added to the reaction mixture. In yet another alternative embodiment, the purge gas may be continuously or intermittently introduced to the reaction mixture from a period of time just before introduction of the carbonylation reagent until vacuum stripping of the excess carbonylation reagent and the solvent or solvent system is complete, as described below.

Regardless of whether the purge gas is continuously or intermittently introduced to the reaction mixture during the reaction of carbonylation reagent and the amino acid (or salt or derivative thereof), it is generally preferred that the purge gas be introduced at a rate and in a manner to provide a reaction product (i.e., a mixture containing solvent and N-carboxyanhydride) containing no more than 0.1% by weight HCl; moreover, it is generally preferred that the purge gas be introduced in a manner and at a rate to maintain the concentration of HCl at 0.1% by weight, or less, during the reaction. In a preferred embodiment, the concentration of HCl is no more than 0.05% by weight in the reaction product.

Typically, the relative rate of addition of the purge gas and phosgene to the reaction mixture is between about 0.15:1 and about 0.4:1 on a molar basis, respectively. More preferably, the relative rate of addition is about 0.28:1, on a molar basis, respectively. If diphosgene or triphosgene are selected as the carbonylation reagent, the relative rates on a molar basis over the period of time at which the purge gas and the carbonylation reagent are added to the reaction mixture, will change by a factor of two or three, respectively. In addition, where mixtures of phosgene, diphosgene and/or triphosgene are employed, the rates and times of introduction to the reaction mixture are adjusted according to the ratios of carbonylation reagents used.

The HCl by-product formed by the reaction of the amino acid or a salt thereof and the solvent or solvent system is volatilized and carried out of the reaction mixture by the purge gas. After the purge gas passes through the reaction mixture, it is treated to remove or reduce the concentration of the carbonylation reagent that will typically be carried by the purge gas (in addition to chloride). Preferably, the purge gas is treated using a chemical scrubber to neutralize the carbonylation reagent and/or a condenser to condense the carbonylation reagent from the purge gas. Where the amount of carbonylation reagent introduced to the reaction mixture exceeds 1 mole, the purge gas is preferably treated using a condenser first, followed by a chemical scrubber.

If the treatment apparatus uses a condensing approach, the purge gas is passed through a condenser to remove the carbonylation reagent from the purge gas. Preferably, the purge gas is cooled to a temperature of about −50° C., or less. More preferably, the purge gas is cooled using a glass dry ice/acetone reflux condenser maintained at a temperature of about −78° C. In a preferred embodiment, condensed carbonylation reagent is reintroduced to the reaction mixture as a liquid.

If the treatment apparatus uses a scrubbing approach, the purge gas is passed through a scrubber, which chemically neutralizes the carbonylation reagent in the purge gas. Typically, such a scrubber comprises a packed column with the purge gas moving countercurrent to a base dissolved in water. Preferably, the base is selected from the group consisting of ammonium hydroxide, potassium hydroxide, sodium hydroxide, and combinations thereof. In a preferred embodiment, the base is sodium hydroxide.

Upon completion of the reaction of the amino acid or a salt thereof with the carbonylation reagent, the solvent or solvent system and the carbonylation reagent are preferably removed by vacuum stripping, leaving a concentrated oily or crystallized residue. In one embodiment, the purge gas is continuously or intermittently introduced to the reaction mixture during vacuum stripping of the solvent or solvent system and the carbonylation reagent from the reaction mixture. In a preferred embodiment, a solvent is then added to the resulting oily or crystallized residue, the solution is vacuum filtered to remove insoluble solids, and an anhydrous non-solvent is added to precipitate the product to form a slurry. The slurry is preferably stirred for 30 minutes and refrigerated overnight. The product may then be isolated by vacuum filtration under a nitrogen blanket, washed first with a mixture of a solvent and a non-solvent (i.e., a liquid in which the N-carboxyanhydride product will not dissolve to any appreciable extent), and then with a non-solvent, partially dried in the funnel by pulling a vacuum while maintaining a positive nitrogen purge for 30 minutes, and then vacuum dried to a constant weight. Preferably, the solvent and the non-solvent described in the preceding filtration and precipitation steps are ethyl acetate and hexanes, respectively.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLE 1

Preparation of L-Glutamic Acid
N-Carboxyanhydride, γ-Ethyl Ester

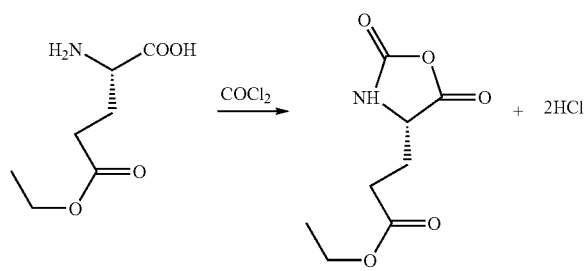

In this Example, a stirred mixture of 30 liters anhydrous tetrahydrofuran and 5,000 g (28.54 moles) L-glutamic acid, γ-ethyl ester, which had been vacuum dried over 500 g sodium hydroxide pellets, was purged with nitrogen below liquid surface at 0.5 liters/min and 25° C. for 30 minutes. The nitrogen purge was increased to 4 liters/min and 5,650 g (57.08 moles) gaseous phosgene was added at 25° C. over 1.5 hours. The phosgene was refluxed back into the reaction vessel using a dry ice/acetone reflux condenser and the reaction exotherm was allowed to increase the reaction mixture temperature up to 60° C. After the phosgene was added, the reaction mixture was heated at 50°-60° C. for 15 minutes until the solids disappeared and a clear solution resulted. The dry ice and acetone were removed from the reflux condenser and the reaction mixture was purged with nitrogen at 4 liters/min and 50°-55° C. for 30 minutes. The tetrahydrofuran and excess phosgene were removed by vacuum stripping at 35°-55° C. down to 2 mm Hg. The concentrated oily residue was mixed with 14.2 liters anhydrous ethyl acetate and the solution vacuum filtered to remove insoluble solids. Anhydrous hexanes (45.0 liters) were added gradually with stirring to the filtrate to crystallize the product. The product slurry was stirred for 30 minutes and refrigerated at 5° C. overnight. The product was isolated by vacuum filtration under a nitrogen blanket, washed with a 7.5 liter solution of 4:1, hexanes:ethyl acetate and with 7.5 liters hexanes, dried in the funnel by pulling vacuum on it for 30 minutes while maintaining a positive nitrogen purge and vacuum dried at room temperature to a constant weight. After drying, 3,893 g (67.8% yield) L-glutamic acid N-carboxyanhydride, γ-ethyl ester were produced with a melting point of 71°-72° C. and a chloride content of 0.020%.

EXAMPLE 2

Preparation of L-Glutamic Acid
N-Carboxyanhydride, γ-Benzyl Ester

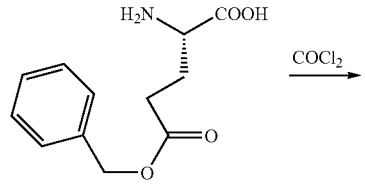

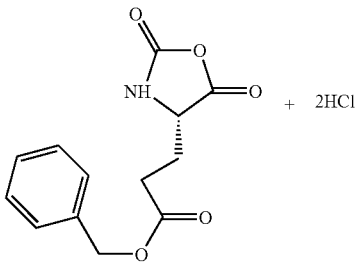

In this Example, a stirred mixture of 3.3 liters anhydrous tetrahydrofuran and 466 g (1.96 moles) L-glutamic acid, γ-benzyl ester, was purged with nitrogen below liquid surface at 0.5 liters/min and heated to 45° C. over 30 minutes. The nitrogen purge was increased to 2 liters/min and 389 g (3.93 moles) gaseous phosgene was added at a rate to maintain a reaction mixture temperature of 50°-65° C. over 10 minutes. The phosgene was refluxed back into the reaction vessel using a dry ice/acetone reflux condenser. After the phosgene was added, the reaction mixture was heated at 50°-65° C. for 25 minutes until the solids disappeared and a clear solution resulted. The dry ice and acetone were removed from the reflux condenser and the reaction mixture was purged with nitrogen at 4 liters/min and 50°-65° C. for 30 minutes. The tetrahydrofuran and excess phosgene were removed by vacuum stripping at 50°-65° C. down to 15 mm Hg whereupon the concentrated residue crystallized. The stripped residue was dissolved in 2.8 liters anhydrous ethyl acetate and the cloudy mixture vacuum filtered to remove insoluble solids. Anhydrous hexanes (5.5 liters) were added gradually with stirring to the filtrate to crystallize the product. The product slurry was stirred for 30 minutes and refrigerated at 5° C. overnight. The product was isolated by vacuum filtration under a nitrogen blanket, washed with a 0.93 liter solution of 3:1, hexanes:ethyl acetate and with 1.4 liters hexanes, dried in the funnel by pulling vacuum on it for 30 minutes while maintaining a positive nitrogen purge and vacuum dried at room temperature to a constant weight. After drying, 461 g (89.2% yield) L-glutamic acid N-carboxyanhydride, γ-benzyl ester were produced with a melting point of 92°-94° C. and a chloride content of 0.022%.

EXAMPLE 3

Preparation of N6-CBZ-L-Lysine
N-Carboxyanhydride

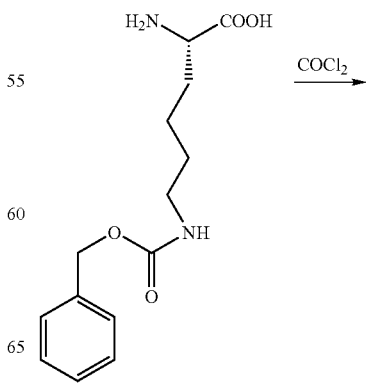

-continued

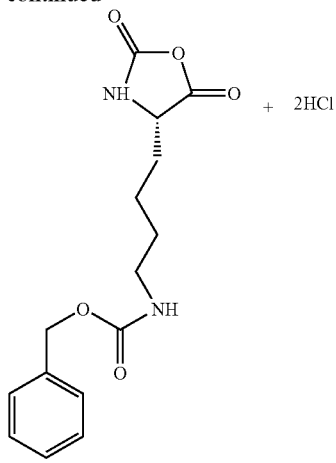 + 2HCl

In this Example, a stirred mixture of 3.2 liters anhydrous tetrahydrofuran and 400 g (1.42 moles) N6-CBZ-L-lysine, was purged with nitrogen below liquid surface at 0.5 liters/min and heated to 50° C. over 30 minutes. The nitrogen purge was increased to 2 liters/min and 282 g (2.85 moles) gaseous phosgene was added at a rate to maintain a reaction mixture temperature of 50°-65° C. over 5 minutes. The phosgene was refluxed back into the reaction vessel using a dry ice/acetone reflux condenser. After the phosgene was added, the reaction mixture was heated at 50°-65° C. for 15 minutes until the solids disappeared and a clear solution resulted. The dry ice and acetone were removed from the reflux condenser and the reaction mixture was purged with nitrogen at 4 liters/min and 50°-65° C. for 30 minutes. The tetrahydrofuran and excess phosgene were removed by vacuum stripping at 50-65° C. down to 100 mm Hg whereupon the concentrated residue crystallized. The stripped residue was dissolved in 2.4 liters anhydrous ethyl acetate with warming up to 30° C. and the cloudy mixture vacuum filtered to remove insoluble solids. 3.2 liters cold (5° C.), anhydrous hexanes were added gradually with stirring to the filtrate to crystallize the product. The product slurry was stirred for 30 minutes and refrigerated at 5° C. overnight. The product was isolated by vacuum filtration under a nitrogen blanket, washed with a 0.8 liter solution of 4:1, hexanes:ethyl acetate and with 0.8 liters hexanes, dried in the funnel by pulling vacuum on it for 30 minutes while maintaining a positive nitrogen purge and vacuum dried at room temperature to a constant weight. After drying, 380 g (87.0% yield) N6-CBZ-L-lysine N-carboxyanhydride were produced with a melting point of 98°-100° C. and a chloride content of 0.082%.

What is claimed is:

1. A process for the preparation of an N-carboxyanhydride, the process comprising:
   forming a reaction mixture comprising an amino acid or a salt thereof, a solvent, and a carbonylation reagent selected from the group consisting of phosgene, diphosgene, triphosgene and mixtures thereof whereby the carbonylation reagent reacts with the amino acid or a salt thereof to yield an N-carboxyanhydride as a product and HCl as a by-product,
   purging the HCl by-product from the reaction mixture by passing a purge gas through the reaction mixture as the carbonylation reagent is reacting with the amino acid or a salt thereof, and
   treating the purge gas after it has passed through the reaction mixture to reduce the concentration of carbonylation reagent therein.

2. The process according to claim 1 wherein the carbonylation reagent is phosgene.

3. The process according to claim 2 wherein the purge gas is a gas selected from the group consisting of nitrogen, helium, argon, neon, and mixtures thereof.

4. The process according to claim 2 wherein the purge gas is predominantly nitrogen.

5. The process according to claim 2 wherein the solvent is selected from the group consisting of tetrahydrofuran, dioxane, diethyl ether, isopropyl ether, dichloromethane, chloroform, 1,2-dichloroethane, N,N'-dimethylformamide, acetonitrile, acetone, ethyl acetate, and combinations thereof.

6. The process according to claim 3 wherein the solvent is selected from the group consisting of tetrahydrofuran, dioxane, diethyl ether, isopropyl ether, dichloromethane, chloroform, 1,2-dichloroethane, N,N'-dimethylformamide, acetonitrile, acetone, ethyl acetate, and combinations thereof.

7. The process according to claim 2 wherein the carbonylation reagent is introduced into the reaction mixture in the form of a liquid.

8. The process according to claim 2 wherein the amino acid is selected from the group consisting of the γ-benzyl ester of glutamic acid, the γ-ethyl ester of glutamic acid, and N6-CBZ-L-lysine and their salts.

9. The process according to claim 6 wherein the amino acid is selected from the group consisting of the γ-benzyl ester of glutamic acid, the γ-ethyl ester of glutamic acid, and N6-CBZ-L-lysine and their salts.

10. The process according to claim 3 wherein the purge gas is treated by passing the purge gas through a condenser to condense the carbonylation reagent from the purge gas.

11. The process according to claim 6 wherein the purge gas is treated by passing the purge gas through a condenser to condense the carbonylation reagent from the purge gas.

12. The process according to claim 9 wherein the purge gas is treated by passing the purge gas through a condenser to condense the carbonylation reagent from the purge gas.

13. The process according to claim 10 wherein the purge gas is further treated by passing the purge gas through a scrubber which neutralizes the carbonylation reagent in the purge gas after the purge gas is passed through the condenser.

14. The process according to claim 11 wherein the purge gas is further treated by passing the purge gas through a scrubber which neutralizes the carbonylation reagent in the purge gas after the purge gas is passed through the condenser.

15. The process according to claim 12 wherein the purge gas is further treated by passing the purge gas through a scrubber which neutralizes the carbonylation reagent in the purge gas after the purge gas is passed through the condenser.

16. The process according to claim 3 wherein the purge gas is treated by passing the purge gas through a scrubber which neutralizes the carbonylation reagent in the purge gas.

17. The process according to claim 6 wherein the purge gas is treated by passing the purge gas through a scrubber which neutralizes the carbonylation reagent in the purge gas.

18. The process according to claim 9 wherein the purge gas is treated by passing the purge gas through a scrubber which neutralizes the carbonylation reagent in the purge gas.

19. The process according to claim 13 wherein the carbonylation reagent is neutralized with a base selected from the group consisting of ammonium hydroxide, potassium hydroxide, sodium hydroxide and combinations thereof.

20. The process according to claim 14 wherein the carbonylation reagent is neutralized with a base selected from the group consisting of ammonium hydroxide, potassium hydroxide, sodium hydroxide and combinations thereof.

21. The process according to claim 15 wherein the carbonylation reagent is neutralized with a base selected from the group consisting of ammonium hydroxide, potassium hydroxide, sodium hydroxide and combinations thereof.

22. The process according to claim 16 wherein the carbonylation reagent is neutralized with a base selected from the group consisting of ammonium hydroxide, potassium hydroxide, sodium hydroxide and combinations thereof.

23. The process according to claim 17 wherein the carbonylation reagent is neutralized with a base selected from the group consisting of ammonium hydroxide, potassium hydroxide, sodium hydroxide and combinations thereof.

24. The process according to claim 19 wherein the base is sodium hydroxide.

25. The process according to claim 23 wherein the base is sodium hydroxide.

26. The process according to claim 3 wherein the purge gas and the carbonylation reagent are added over a period of time, wherein the average relative rate of addition on a molar basis over the period of time is between 0.15:1 and 0.4:1, respectively.

27. The process according to claim 12 wherein the purge gas and the carbonylation reagent are added over a period of time, wherein the average relative rate of addition on a molar basis over the period of time is between 0.15:1 and 0.4:1, respectively.

28. The process according to claim 3 wherein the N-carboxyanhydride product is recovered and the product contains less than 0.1% by weight HCl.

29. The process according to claim 12 wherein the N-carboxyanhydride product is recovered and the product contains less than 0.1% by weight HCl.

30. The process according to claim 26 wherein the N-carboxyanhydride product is recovered and the product contains less than 0.1% by weight HCl.

* * * * *